United States Patent
Jeglorz et al.

(10) Patent No.: US 8,382,781 B2
(45) Date of Patent: Feb. 26, 2013

(54) DEVICE FOR OPHTHALMIC SURGERY

(75) Inventors: Tobias Jeglorz, Nürnberg (DE); Christof Donitzky, Eckental/Eschenau (DE)

(73) Assignee: Wavelight GmbH, Erlangen (DE)

( * ) Notice: Subject to any disclaimer, the term of this patent is extended or adjusted under 35 U.S.C. 154(b) by 233 days.

(21) Appl. No.: 12/894,341

(22) Filed: Sep. 30, 2010

(65) Prior Publication Data

US 2012/0083812 A1 Apr. 5, 2012

(51) Int. Cl.
*A61F 9/00* (2006.01)

(52) U.S. Cl. .......................................................... 606/166

(58) Field of Classification Search ................... 606/107, 606/115, 161, 162, 166; 417/5, 14, 43; 137/565.33
See application file for complete search history.

(56) References Cited

U.S. PATENT DOCUMENTS

| | | | | |
|---|---|---|---|---|
| 5,651,782 | A * | 7/1997 | Simon et al. ....................... | 606/1 |
| 5,971,981 | A | 10/1999 | Hill et al. | |
| 6,059,805 | A * | 5/2000 | Sugimura et al. .............. | 606/166 |
| 6,506,198 | B1 | 1/2003 | Amano | |
| 6,592,601 | B1 * | 7/2003 | Toh et al. ....................... | 606/166 |
| 7,166,117 | B2 * | 1/2007 | Hellenkamp .................. | 606/166 |
| 2002/0198553 | A1 * | 12/2002 | Schumer et al. .............. | 606/166 |
| 2003/0045895 | A1 * | 3/2003 | Ross et al. ..................... | 606/166 |
| 2003/0078487 | A1 * | 4/2003 | Jeffries et al. ................. | 600/398 |
| 2005/0049621 | A1 * | 3/2005 | Feingold et al. .............. | 606/166 |
| 2006/0069402 | A1 * | 3/2006 | Sugimura ..................... | 606/166 |

FOREIGN PATENT DOCUMENTS

| | | |
|---|---|---|
| EP | 0836868 A2 | 4/1998 |
| WO | 02/087451 A1 | 11/2002 |
| WO | 2007/006433 A1 | 1/2007 |

* cited by examiner

*Primary Examiner* — Ryan Severson
*Assistant Examiner* — David Eastwood
(74) *Attorney, Agent, or Firm* — Keiko Ichiye

(57) ABSTRACT

A device for ophthalmic surgery includes a vacuum-pump arrangement for generating a vacuum serving for fixing a suction ring to an eye, an evacuation-path system for transmitting the vacuum to an interface port which permits the separable attachment of a suction-ring instrumentarium including the suction ring, and also a control unit for controlling the vacuum-pump arrangement. In accordance with the invention, the device includes pressure-measuring components for measuring at least the vacuum pressure, the control unit adapted to ascertain a differential pressure between the measured vacuum pressure and an atmospheric pressure. The vacuum-pump arrangement is preferably operated at maximal pumping power in a test-operation mode with suction-ring instrumentarium not attached, in order to ascertain an optimally obtainable relative underpressure in the evacuation-path system. In this way, in the case of fluctuating altitudes of the location of use of the ophthalmic-surgery device and also in the case of fluctuating weather conditions (low pressure, high pressure) it can be ascertained at all times whether the achievable relative underpressure is sufficient.

12 Claims, 1 Drawing Sheet

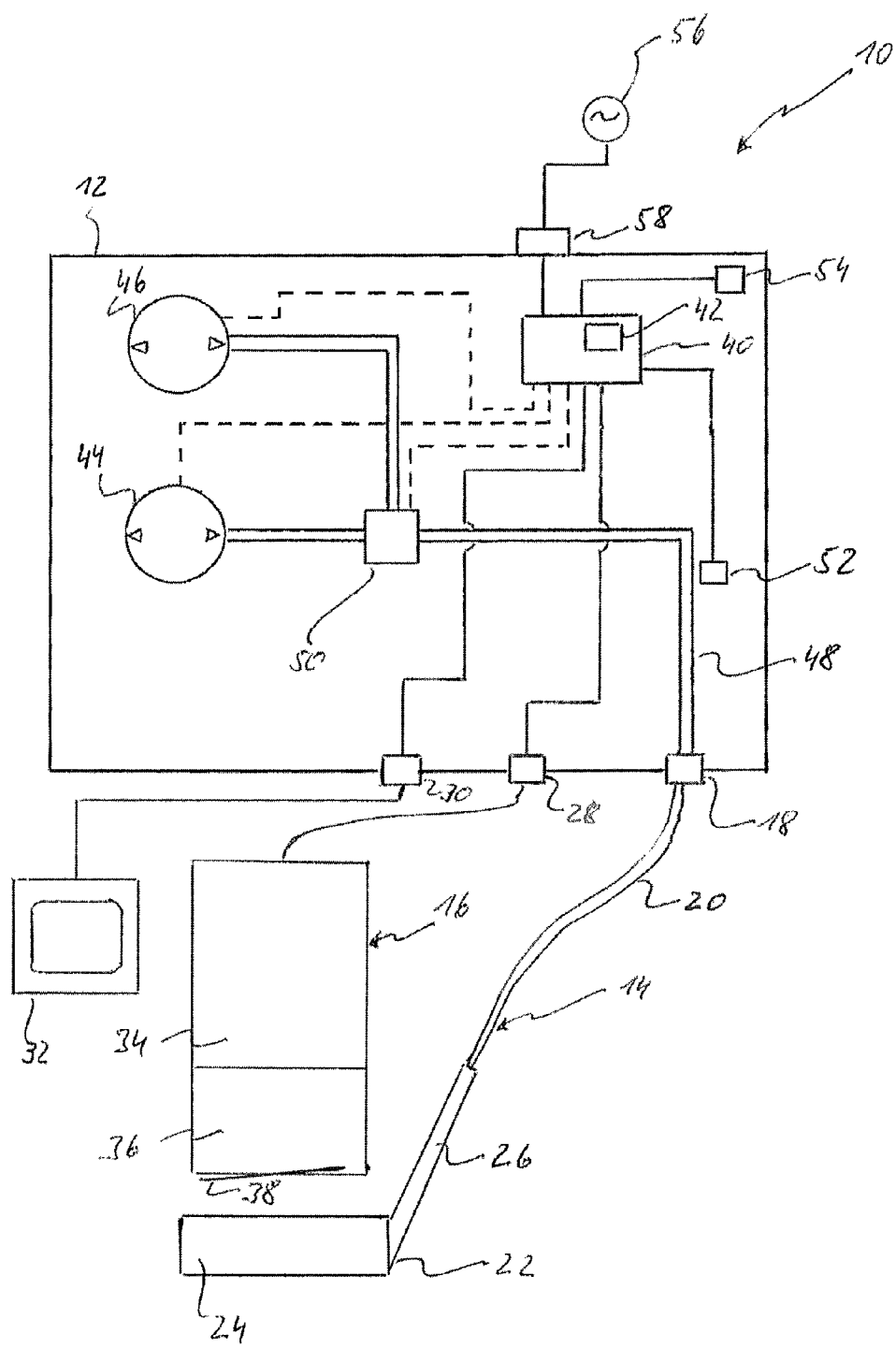

DEVICE FOR OPHTHALMIC SURGERY

The invention relates to a device for ophthalmic surgery, including a vacuum-pump arrangement for generating a vacuum serving for fixing a suction ring to an eye, an evacuation-path system for transmitting the vacuum to an interface port which permits the separable attachment of a suction-ring instrumentarium including the suction ring, and also a control unit for controlling the vacuum-pump arrangement.

BACKGROUND OF THE INVENTION

A device of such a type may come into operation, for example, within the scope of a microkeratome, i.e. in the case of a microsurgical plane such as is used, for example, for the placement of a flap incision on a human eye. Such a flap incision is necessary within the scope of a form of operation customarily known in specialist circles as LASIK (laser in-situ keratomileusis). By means of the flap incision, in this case on the surface of the cornea a small disc (flap) is cut out which on a part of its periphery is still connected to the remaining corneal tissue and can therefore be folded aside and subsequently folded back again without difficulty. Depending on whether the flap incision extends within the stroma or within the epithelium on Bowman's membrane, in specialist circles one customarily speaks of classical LASIK or Epi-LASIK, respectively.

In the case of a microkeratome, the suction ring is needed not only for the purpose of fixing the eye but customarily also for the purpose of coupling and guiding a cutting unit equipped with a cutting blade, which, as a rule, is held in the hand by the operating surgeon and is therefore frequently also designated as a handpiece of the microkeratome. Also customarily part of the handpiece is a motorised drive unit which serves for generating the cutting motion of the cutting blade. In the case of a microkeratome marketed by WaveLight under the trade name RONDO, the cutting blade has, like a razor, a rectilinear cutting edge and is moved linearly, subject to high-frequency lateral oscillation, in the direction perpendicular to the cutting edge. The cutting blade is, for example, held in a cutting head which is separably and consequently interchangeably coupled with a drive module of the handpiece.

The suction-ring instrumentarium may include, in addition to the actual suction ring, further components which, for example, serve for transmitting the vacuum from the interface port to the suction ring. For example, these components may include a hose line with a suitable connector for connecting to the interface port. At the end remote from the interface this hose line may have been separably connected to a connecting piece of a suction-ring unit forming the suction ring and, for example, produced in one piece. It should be pointed out that the suction-ring unit may perfectly well exhibit several hose-line ports which permit the attachment of several hose lines, particularly if the suction-ring unit exhibits several evacuation spaces (suction chambers) that are capable of being evacuated separately. For the purpose of fixing the suction ring to the eye, said suction ring customarily exhibits an annular chamber delimited exclusively between the suction ring and the surface of the eye.

A device according to the invention may, alternatively or additionally, come into operation within the scope of a cutting machining of the human eye using laser technology. Relevant laser systems often provide for the interposition of an adapter between the eye to be machined and an objective which focuses the laser radiation onto the eye. The adapter brings about a positioning of the eye in relation to the laser system, facilitating the accurately targeted generation of the incision. In this connection it is known to construct the adapter with a contact element that is transparent to the laser radiation and that is brought into planar contact with the eye. In the case of a plane contact surface of the contact element, a levelling of the cornea takes place; one therefore speaks of an applanation element.

By reciprocal coupling of the suction ring, which in turn is firmly aspirated on the eye, and of the adapter, for instance by aspirating the adapter onto the suction ring, it is possible to position the eye precisely and securely in relation to the laser system.

Regardless of the form of the operation in which the suction-ring instrumentarium is being employed, a sufficiently intense vacuum is necessary, in order that the suction ring remains firmly aspirated on the eye reliably during the operation. As a rule, the vacuum-pump arrangement is dimensioned so as to be sufficiently powerful in order to be able to build up the requisite vacuum under normal conditions. An overdimensioning of the vacuum-pump arrangement is of course not desirable as a rule, for reasons of cost and construction space.

The achievable quality of the vacuum depends not only on the maximal pumping power of the vacuum-pump arrangement but also on the altitude of the location of use and on the current weather situation. For given pumping power, the achievable vacuum pressure depends on the current atmospheric pressure at the location of use, in which connection this atmospheric pressure may fluctuate more or less intensely, depending on the altitude of the location of use and depending on the state of the weather (high pressure, low pressure). This may have the consequence that, under certain circumstances, in the case of a location of use situated at a great height only a considerably smaller operating range of the vacuum than under lowland conditions is available. Even if the user presets a certain nominal value of the relative underpressure ('relative underpressure' means the level of the underpressure in relation to the environment) at an operating console, the relative underpressure actually achieved may be substantially lower (e.g. −500 mmHg instead of a value desired by the user of, for example, −600 mmHg) and therefore may under certain circumstances give rise to surgical dangers.

BRIEF SUMMARY OF THE INVENTION

An object of the invention is to develop further an ophthalmic-surgery device of the type designated in the introduction in such a manner that restrictions of the operating range of the vacuum of the vacuum-pump arrangement caused by altitude or weather are detectable.

With a view to achieving this object, the invention proposes to provide the ophthalmic-surgery device with pressure-measuring components for measuring at least the vacuum pressure, in which connection the control unit is adapted to ascertain a differential pressure between the measured vacuum pressure and an atmospheric pressure. Advantageously, the pressure-measuring components are also designed for measuring the atmospheric pressure, so that the control unit can ascertain the differential pressure from the measured vacuum pressure and the measured atmospheric pressure. Alternatively, an input by a user is conceivable, this input being representative of the atmospheric pressure. For example, it is conceivable to store in a memory, in tabular or formulaic form, information about the correspondence between the altitude above sea-level and an associated nominal atmospheric pressure. The user can then enter a specification of the altitude of the location of use, from which the control unit ascertains a value of the atmospheric pressure by accessing the stored information.

Whenever a control of the vacuum-pump arrangement is mentioned here, it will be understood that a closed-loop control in the control-engineering sense is covered thereby. The term 'control' is used here as a general term for both a control without feedback and a control with feedback (closed-loop control).

The control unit is preferably adapted to bring about a test-operation mode of at least one vacuum pump of the vacuum-pump arrangement with a predetermined setting of the pumping power and to ascertain the differential pressure on the basis of one or more values of the vacuum pressure measured during this test-operation mode. The test-operation mode can be initiated by the control unit automatically every time a predetermined trigger arises. Such a trigger is, in particular, the switching-on of an electrical power supply of the control unit and of the vacuum-pump arrangement. If the ophthalmic-surgery device is switched on in the morning and switched off again in the evening, for example in hospital operation, the test-operation mode is implemented once a day, to be specific in the morning after switching on. Of course, it is conceivable, alternatively or additionally, to preset further triggering factors that can cause an implementation of the test-operation mode. For example, the test-operation mode can be started if no test-operation mode has been carried out for a predetermined period.

The test-operation mode is intended to serve to ascertain the relative underpressure actually achieved and, tying in with this, to be able to assess whether a sufficiently high suction force on the suction ring can be generated, in order to be able to carry out an operation reliably. For this purpose it is expedient if the control unit has been set up to implement the test-operation mode without suction-ring instrumentarium attached to the interface port. In particular, the control unit may have been set up to implement the test-operation mode only when the suction-ring instrumentarium is not attached to the interface port. In order, without suction-ring instrumentarium attached, to make available a sealed space in which the vacuum can be generated in the manner of a test, it is conceivable to configure the interface port with a shut-off function which brings about a shutting-off of the evacuation-path system toward the outside if the suction-ring instrumentarium is not attached. By virtue of the attaching of the suction-ring instrumentarium to the interface port, the shut-off function can be cancelled; the vacuum can then pass out of the evacuation-path system into the suction-ring instrumentarium. It will be understood that a shut-off point switching in a manner depending on the attaching of the suction-ring instrumentarium to the interface port may also be situated remote from the interface port in a part of the evacuation-path system situated further inside.

Expediently the test-operation mode involves the setting of a maximal pumping power of at least one pump of the vacuum-pump arrangement. This permits the maximal operating range of the vacuum-pump arrangement that is possible at a given location of use at a given time to be ascertained, i.e. the optimally achievable relative underpressure.

To the extent that the vacuum-pump arrangement includes two (or more) separately operable vacuum pumps, the control unit may be adapted to operate the two vacuum pumps in succession during the test-operation mode and to ascertain a value of the differential pressure for each of the two pumps. The two pumps may, for example, be organised as main pump and auxiliary pump, the auxiliary pump coming into operation when the main pump fails. Since the demands made of the suction force of the suction ring are to be satisfied also after the auxiliary pump has come into operation, within the scope of the test-mode operation it is expedient firstly to operate one of the pumps at maximal pumping power, then to run this pump down and subsequently to operate the other pump likewise at maximal pumping power. This permits any differences in power—and accordingly differences in the operating range of the two pumps—to be detected.

In a preferred embodiment of the invention, the control unit is adapted to compare the measured vacuum pressure or/and a quantity ascertained in a manner depending on the measured vacuum pressure with at least one predetermined threshold value and to bring about a predetermined response, depending on the result of the comparison. The predetermined response may include, for example, an operational disabling of at least one component of the ophthalmic-surgery device if the result of the comparison indicates an insufficient vacuum. The component to be disabled may be, for example, a motorised drive unit for a mechanical cutting head of a microkeratome, equipped with a cutting blade. Alternatively it may be, for example, a laser-source which upon establishment of an insufficient achievable vacuum is disabled by the control unit so as to avoid the emission of laser radiation.

The predetermined response may, alternatively or in supplement, include the output of a visually or/and acoustically perceptible warning indication if the result of the comparison indicates an insufficient vacuum. The warning indication may, for example, be output in the form of a text message on a monitor, or it may consist in a signal lamp being activated in accordance with a predetermined pattern (e.g. flashing or continuous illumination).

The control unit is preferably adapted to compare the differential pressure or/and a pressure value that has been reduced by a predetermined amount in relation to the differential pressure with at least one predetermined threshold value. By a pressure value that has been reduced in relation to the differential pressure being made the basis of the comparison, there is a certain safety margin, within which the maximally achievable vacuum may fluctuate without being judged to be no longer sufficient. The predetermined amount may be, for example, a percentage reduction; an absolute reduction is also conceivable.

It has been shown that in many cases a relative underpressure between −350 mmHg and −650 mmHg, preferably between −550 mmHg and −600 mmHg, is regarded as necessary and desirable for a reliable adhesion of the suction ring on the eye. Accordingly, it is preferred to establish a threshold value within this range. An establishment by the manufacturer without possibility of amendment by the user is conceivable in this connection. Alternatively or additionally, at least one threshold value may be capable of being set by the user.

DETAILED DESCRIPTION OF PREFERRED EMBODIMENTS

The invention will be elucidated further in the following on the basis of the appended drawing. FIG. 1 thereof represents schematically an embodiment of an ophthalmic-surgery device 10, which in the exemplary case that is shown takes the form of a microkeratome. The microkeratome serves for generating a corneal flap on a human eye, which is not represented in any detail, within the scope of a LASIK operation or Epi-LASIK operation. The microkeratome 10 includes a control console 12 which is expediently configured as a table-mounted instrument, a suction-ring instrumentarium 14 and also a cutting handpiece 16. For the purpose of attaching the suction-ring instrumentarium 14 to the control console 12, the latter exhibits a vacuum interface port 18, to which a hose line 20 of the suction-ring instrumentarium 14 is capable of being separably attached. The suction-ring instrumentarium 14 furthermore exhibits a suction-ring unit 22—for example, produced in one piece from a light metal, for example titanium—with a suction ring 24 and also with a connecting piece 26 protruding from said suction ring, to which the hose line 20 is preferably separably connected.

Electrical interface ports 28, 30 permit, furthermore, the attachment of the cutting handpiece 16 and also of a external monitor 32 to the control console 12. If desired, the control console 12 may, alternatively or additionally to the external monitor 32, exhibit an integrated display unit (not represented in any detail) for displaying information.

In the exemplary case that is shown, the cutting handpiece 16 is of modular construction and is composed of a drive module 34 and a cutting module 36 separably coupled with said drive module. The cutting module 36 is equipped with an interchangeable cutting blade 38, the cutting edge of which protrudes by an amount determining the thickness of the flap to be generated in relation to an applanation face of the cutting module 36 which is not indicated in any detail and which brings about a levelling of the cornea. The drive module 34 is furnished with motorised drive components, in order, on the one hand, to cause the cutting blade 38 within the cutting module 36 to perform high-frequency lateral oscillation and, on the other hand, to move the cutting handpiece 16 as a whole back and forth in a linear direction in relation to the suction ring 24. For example, the suction-ring unit 22 may exhibit serrated guide tracks into which pinions arranged on the cutting module 36 and driven by the drive module 34 engage in intermeshing manner.

The control console 12 contains a processor-based control unit 40 which controls the entire operation of the microkeratome 10 and which operates in accordance with a control program 42. Contained in addition in the control console 12 is a vacuum-pump arrangement which consists, in the exemplary case that is shown, of two vacuum pumps 44, 46 and which serves for generating a vacuum to be conducted via an internal evacuation-path system 48 to the vacuum interface port 18 and from there further to the suction ring 24. In the present embodiment, the vacuum pumps 44, 46 are organised as main pump and auxiliary pump, one of the pumps, for instance pump 44, serving as main pump, and the other, for instance pump 46, being switched in only when required, for example if the main pump 44 fails. A change-over switch 50 permits the optional linkage of the main pump 44 or of the auxiliary pump 46 to the evacuation-path system 48. The two pumps 44, 46 and also the change-over switch 50 are controlled by the control unit 40; this is indicated by dashed connecting lines in FIG. 1. In a modification it is conceivable to dispense with the change-over switch 50, so that the two pumps 44, 46 are permanently connected to the evacuation-path system 48. Given individual controllability of each of the two pumps 44 46, also in this case one of the pumps can be put into operation and the other pump can remain unoperational, at any rate as long as the first pump is functioning properly.

Part of the control console, furthermore, are two pressure sensors 52, 54 which supply their sensor signals to the control unit 40 which ascertains measured pressure values therefrom. Pressure sensor 52 is assigned to the evacuation-path system 48 and measures the vacuum pressure (i.e. the absolute pressure) in the evacuation-path system 48. Pressure sensor 54, on the other hand, serves for measuring the ambient air pressure (atmospheric pressure). The measured pressure values of the two sensors 52, 54 are subjected to a subtraction by the control unit 40, in order to ascertain the relative underpressure in the evacuation-path system 48, i.e. the difference between the ambient air pressure and the generated vacuum pressure in the evacuation-path system 48.

At 56 an electrical mains supply is indicated, from which the microkeratome 10 draws its electrical energy needed for operation. A master switch 58 arranged externally on the control console 12 permits the switching on and off of the control console 12 and hence of the microkeratome 10 as a whole.

The vacuum interface port 18 is constructed, in a manner not represented in any detail, with a suitable shut-off device (e.g. closing flap) which seals the evacuation-path system 48 tightly toward the outside if the hose line 20 of the suction-ring instrumentarium 14 is not attached, i.e. if the interface port 18 is vacant. As a result of the hose line 20 being clipped on, the shut-off device is opened, so that the passageway from the evacuation-path system 48 via the interface port 18 into the hose line 20 is open.

The control program 42 contains instructions that provide for a test-operation mode of the control console 12 after each switching-on of the master switch 58. Within the scope of the test-operation mode, each of the two pumps 44, 46 is started up in succession and operated at maximal pumping power. To the extent that further controllable components are assigned to the evacuation-path system 48, by means of which the intensity of the vacuum in the evacuation-path system 48 is capable of being influenced, these components are also set in such a way within the scope of the test-operation mode that the vacuum prevailing in the evacuation-path system is maximal. An example of such a component may be a point for introduction of extraneous air, with adjustable cross-section for introduction of extraneous air, as described in EP 1 743 609 A1.

Within the scope of the test-operation mode the pumps 44, 46 are operated at maximal pumping power for a sufficient period of time. During the maximal operation the control unit 40 registers, by means of the pressure sensor 52, the vacuum pressure in the evacuation-path system 48; this vacuum pressure consequently represents the optimally obtainable vacuum pressure under the given conditions (altitude of the location of use of the microkeratome 10, current weather situation). By drawing upon the ambient air pressure measured by the pressure sensor 54, the control unit 40 then ascertains the differential pressure between the ambient air pressure and the vacuum pressure and compares this differential pressure with a predetermined threshold which is permanently stored or capable of being set by the user. The ascertained differential pressure represents the optimally achievable relative underpressure under the given conditions. The comparison with the given threshold permits the control unit 40 to establish whether the relative underpressure is sufficient in order to be able to carry out an operation with the microkeratome 10 without risk of a detachment of the suction ring from the eye.

The above comparison is carried out separately for each of the pumps 44, 46, so that the control unit 40 can ascertain, independently for both pumps, the maximal operating range thereof under the given conditions. The test-operation mode preferably only takes place and can only be triggered if the vacuum interface port 18 is vacant—that is to say, if the aforementioned shut-off device is closed. Depending on the result of the test-operation mode, the control unit 40 can bring about differing responses. If the achievable relative underpressure is not sufficient, it is conceivable that the control unit 40 blocks the supply of energy to the cutting handpiece 16 via the electrical interface port 28 and hence renders the cutting handpiece 16 non-operational. Alternatively or additionally, the control unit 40 can output a suitable warning message on the monitor 32. The warning message may contain statements about the achievable relative underpressure, in order that the operating surgeon knows exactly which pressure values he/she can expect.

Expediently, prior to the comparison of the measured differential pressure with the threshold a percentage reduction or absolute reduction is subtracted from the differential pressure. This reduction may serve to take into account any fluctuations in the maximal pumping power of the pumps 44, 46, as well as any measuring inaccuracies.

The threshold considered in the comparison may, for example, be set or capable of being set to −570 mmHg. It will be understood that other numerical values are just as conceivable for the threshold. Expediently, however, the threshold is set or capable of being set within a range between −550 mmHg and −600 mmHg. This corresponds to a relative underpressure such as is frequently regarded as necessary and sufficient for eye operations.

The invention claimed is:

1. A device for ophthalmic surgery, comprising:
   a vacuum-pump arrangement for generating a vacuum serving for fixing a suction ring to an eye,
   an evacuation-path system for transmitting the vacuum to an interface port which permits the separable attachment of a suction-ring instrumentarium including the suction ring,
   a control unit for controlling the vacuum-pump arrangement,
   pressure-measuring components for measuring an atmospheric pressure and a vacuum pressure from the vacuum, the control unit adapted to ascertain a differential pressure between the measured vacuum pressure and the measured atmospheric pressure,
   wherein the control unit is adapted to:
   bring about a test-operation mode of at least one vacuum pump of the vacuum-pump arrangement with a predetermined setting of the pumping power,
   ascertain the differential pressure on the basis of one or more values of the vacuum pressure measured during the test-operation mode, and
   implement the test-operation mode only when the suction-ring instrumentarium is not attached to the interface port.

2. A device according to claim 1, wherein the test-operation mode includes the setting of a maximal pumping power of the at least one vacuum pump of the vacuum-pump arrangement.

3. A device according to claim 1, wherein the control unit is adapted to implement the test-operation mode after each switching-on of an electrical power supply of the control unit and of the vacuum-pump arrangement.

4. A device according to claim 1, wherein the vacuum-pump arrangement includes two separately operable vacuum pumps and the control unit is adapted to operate the two vacuum pumps in succession during the test-operation mode and to ascertain a value of the differential pressure for each of the two pumps.

5. A device according to claim 1, wherein the control unit is adapted to compare the measured vacuum pressure and a quantity ascertained in a manner depending on the measured vacuum pressure with at least one predetermined threshold value and to bring about a predetermined response, depending on the result of the comparison.

6. A device according to claim 5, wherein the control unit is adapted to compare the differential pressure and a pressure value reduced by a predetermined amount in relation to the differential pressure with at least one predetermined threshold value.

7. A device according to claim 6, wherein the at least one predetermined threshold value includes a threshold value of between 350 mmHg and 650 mmHg.

8. A device according to claim 6, wherein the at least one threshold value is capable of being set by the user.

9. A device according to claim 5, wherein the predetermined response includes an operational disabling of at least one component of the ophthalmic-surgery device if the result of the comparison indicates an insufficient vacuum.

10. A device according to claim 9, wherein the operational disabling relates to at least one motorised drive unit for a mechanical cutting unit of a microkeratome equipped with a cutting blade.

11. A device according to claim 5, wherein the predetermined response includes the output of at least one of a visually and an acoustically perceptible warning indication if the result of the comparison indicates an insufficient vacuum.

12. A device according to claim 1, wherein the pressure-measuring components comprise:
   a first pressure sensor configured to measure the vacuum pressure of the evacuation-path system; and
   a second pressure sensor configured to measure the atmospheric pressure.

* * * * *